United States Patent [19]

Hayashi et al.

[11] Patent Number: 4,906,612
[45] Date of Patent: Mar. 6, 1990

[54] METHOD FOR ANIMAL GROWTH PROMOTION USING GLYCLOPEPTIDES

[75] Inventors: Yoshiyuki Hayashi, Kusatsu; Takao Konishi, Ikeda; Koichi Matsumoto, Toyonaka, all of Japan

[73] Assignee: Shionogi & Co., Ltd., Osaka, Japan

[21] Appl. No.: 303,745

[22] Filed: Jan. 25, 1989

[30] Foreign Application Priority Data

Jan. 26, 1988 [JP] Japan .................................. 63-15341

[51] Int. Cl.$^4$ ............................................. A61K 37/00
[52] U.S. Cl. .......................................... 514/8; 530/322
[58] Field of Search ............................. 514/8; 530/322

[56] References Cited

U.S. PATENT DOCUMENTS

| | | | |
|---|---|---|---|
| 4,537,879 | 8/1985 | Hamill et al. | 514/9 |
| 4,557,933 | 12/1985 | Haneishi et al. | 435/169 |
| 4,558,036 | 12/1985 | Merkel | 514/9 |
| 4,637,981 | 1/1987 | Hershberger et al. | 435/78 |
| 4,659,660 | 4/1987 | Hamill et al. | 435/71 |
| 4,742,045 | 5/1988 | Verma et al. | 514/8 |

Primary Examiner—Lester L. Lee
Attorney, Agent, or Firm—Wenderoth, Lind & Ponack

[57] ABSTRACT

An agent for animal growth promotion which comprises, as an essential component, a compound of the formula I:

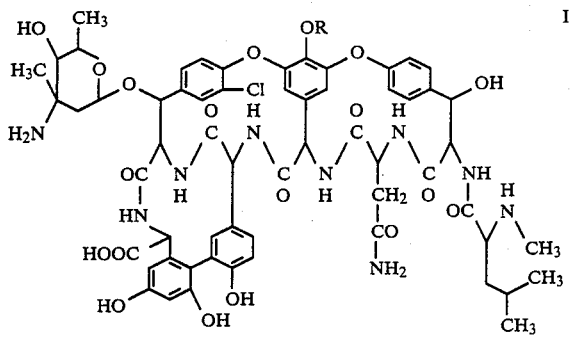

wherein R is

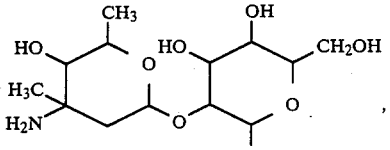

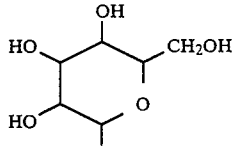

or H, or a salt thereof. A method for growth promotion of animals is also provided.

1 Claim, No Drawings

METHOD FOR ANIMAL GROWTH PROMOTION USING GLYCLOPEPTIDES

The present invention relates to a novel agent which comprises a glycopeptide compound and a salt thereof. More particularly, the invention relates to an agent for animal growth promotion which comprises, as an essential component, a compound of the formula I:

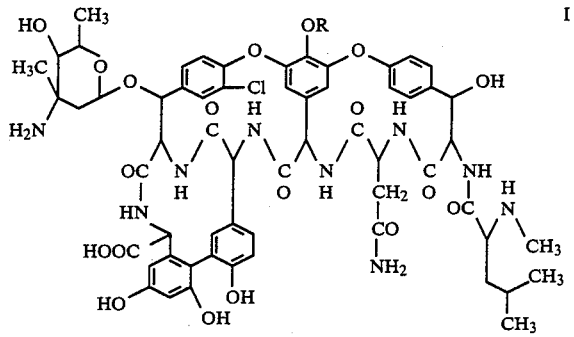

wherein R is

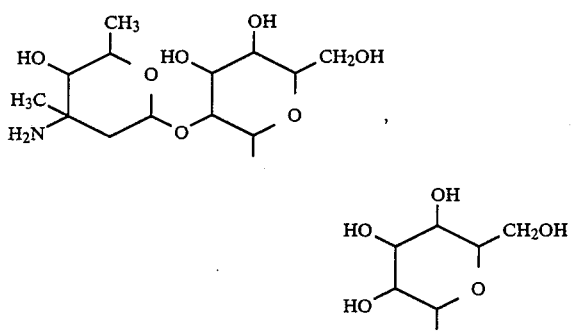

or H, and salts thereof. The invention also relates to a method for growth promotion of animals, which comprises administering an effective amount of a compound of the above formula I or a salt thereof in admixture with conventional carriers and/or ingredients for an animal feed.

There have hitherto been known many glycopeptide antibiotics, including vancomycin and their derivatives. Also, it is well known that the administration of these antibiotics to animals promotes the growth of the animals: For instance, Japanese Patent Publication Nos. 129693/1982, 213394/1984, 213395/1984, 502335/1986, 122300/1986, 126970/1987, 199397/1985, 237099/1985, 231698/1985, and 251699/1986; U.S. Pat. Nos. 4558036 and 4537770; European Patent Publication No. 119575; and so forth.

Of the compounds according to the present invention, the compound of the above formula I wherein R is

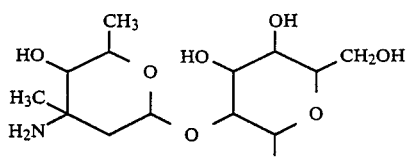

is known and disclosed as PA-42867-A in Japanese Patent Publication No. 174099/1987, and the compound of the above formula I wherein R is

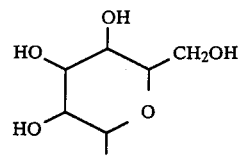

or H is also known and disclosed as des-(4-epi-vancosaminyl) PA-42867-A or des-(4-epi-vancosaminyl-0-glucosyl)PA-42867-A in Japanese patent application No. 188865/1986.

Presently, several growth promoting compounds for animals including Thiopeptin, etc. are commercially available.

As stated above, it has been also known that some of vancomycin antibiotics have a growth-promoting action on animals. However, nothing has been known about the growth-promoting action of the compounds according to the present invention.

BRIEF DESCRIPTION OF THE INVENTION

The inventors have found that the abovementioned compounds have a strong antibacterial activity on strains belonging to genus *Clostridium*, said activity being helpful for evaluating the growth-promoting action of the compounds, and also found that the application of the said compounds to animals leads to a remarkable increase in body weight of the animals. Thus, the present invention relates to the novel use of the glycopeptide compounds of the above formula I and salts thereof, as a growth promoter for animals. Furthermore, the invention provides an agent for animal growth promotion, which comprises as an essential active ingredient an effective amount of a compound of the above formula I or a salt thereof in admixture with conventional carriers and/or ingredients for an animal feed.

DETAILED DESCRIPTION OF THE INVENTION

Although one or more of the glycopeptide compounds per se according to the present invention may be applied directly to animals by, for example, oral administration, they are often applied in the form of a premix which is prepared by mixing the glycopeptide(s) with conventional carriers such as defatted rice bran, defatted soybean flour, bran, kaolin, talc, calcium carbonate, lactose, water, etc. More preferably, such premix or the glycopeptide compounds per se is applied to animals after mixing with conventional animal feeds. Thus, the preferred embodiment of the agent of the present invention is an animal feed ration for growth promotion, and therefore, the subsequent explanation will preferentially be directed to the animal feed containing the above-mentioned glycopeptide compounds.

The glycopeptide compounds used here are not necessarily required to be pure materials; for instance, a culture medium in which glycopeptides-producing microorganism has been cultured can be employed as a whole after partial purification. Veterinaryly acceptable salts of the glycopeptides may also be used, and include, for example, salts with alkali metals such as potassium and sodium; salts with alkaline-earth metals such as magnesium and aluminium; salts with inorganic acids such as hydrochloric acid, sulfuric acid and nitric acid; and salts with organic acids such as acetic acid and fumaric acid.

For the preparation of the animal feed which contains one or more of the glycopeptides according to the present invention, any material usually used as a feed component for animals may be employed. Examples of such material are corn, bran, rice, wheat or barley, cotton seed meal, milo, soybean meal, fish meal, defatted rice bran, oil and fat, alfalfa, calcium carbonate, calcium phosphate, sodium chloride, choline chloride, vitamins such as vitamin A, vitamin D, vitamin E, vitamin $B_1$, vitamin $B_2$, vitamin $B_6$, vitamin $B_{12}$, calcium pantothenate, nicotinamide and folic acid, inorganic salts such as magnesium sulfate, iron sulfate, copper sulfate, zinc sulfate, potassium iodide and cobalt sulfate. All or part of these materials may be mixed with one or more of the glycopeptides. Besides, other antibiotics, bactericides, anti-coccidium agents, vermifuges and the like may also be added.

The growth-promoting agent according to the invention may be used for various animals. Examples of such animals are poultry and domestic animals, including chicken, turkey, duck, quail, cow, horse, pig, sheep, goat, mink, rabbits and the like. These animals may be raised in a conventional manner.

The daily dosage of one or more of the glycopeptides according to the present invention ranges from 0.01 to 3.0 mg per kg of the body weight of an animal, irrespective of the fact that the glycopeptide(s) per se is used, or a microorganism culture containing the glycopeptides is used, or an extracted crude material containing the glycopeptides is used. The dosage of from 0.3 to 3.0 mg/kg/day is preferred for poultry, while the dosage of from 0.01 to 1.0 mg/kg/day is preferred for cattle and swine. The content of the glycopeptide(s) according to the invention in an animal feed will generally range from 0.5 ppm to 100 ppm.

The growth-promoting agent of the present invention not only promotes the growth of animals, but also improves feed utilization efficiency. The agent is also effective for the treatment of bacterial diseases. Moreover, its toxicity in animals is low, and it does not remain at all in animal bodies, which are advantageous characteristics of the agent of the invention. $LD_{50}$ values of the compounds according to the present invention when intravenously injected in male mice are shown below:

| Compounds | $LD_{50}$ (mg/kg) |
| --- | --- |
| PA-42867-A | 1955 |
| Des-(4-epi-vancosaminyl)PA-42867-A | >3000 |
| Des-(4-epi-vancosaminyl-O—glucosyl)PA-42867-A | 205 |

The method of preparing the compounds according to the present invention is described in detail in Japanese Patent Publication (not examined) No. 174099/1987 and Japanese patent application No. 188865/1986, and can be prepared as follows:

(a) Fermentation Step:

Seed slant culture of *Nocardia* sp. PA-42867 (FERM BP-1230) is inoculated into an Erlenmeyer flask (2 L) charged with 800 ml of the broth comprising 0.5% soluble starch, 0.5% glucose, 0.5% polypeptone, 0.5% meat ext., 0.25% yeast ext., 0.25% sodium chloride, and deionized water (pH 7.0 before sterilization), and fermented with shaking at 180 r.p.m. at 28° C. for 48 hours. This fermented broth (800 ml) is transplanted into a jar-fermenter (30 L) charged with 20 L of the same broth as noted above, and fermented at 28° C. for 24 hours with stirring at 200 r.p.m. (aeration rate 20 L/min., and internal pressure 0.5 $Kg/cm^2G$). Then, 10 L of the resulting broth is transplanted into a fermentation tank (250 L) charged with 140 L of the broth comprising 2.4% tomato paste, 2.4% dextrin, 1.2% dried yeast (Beast, Iwaki Seiyaku Co., Ltd.), 0.0006% cobalt chloride hexahydrate, 0.08% defoamer P-2000 (Dai Nippon Ink & Chemicals Inc.) and tap water (pH 7.0 before sterilization), and fermented at 28° C. for 64 hours with stirring at 325 r.p.m. (aeration rate 150 L/min., and internal pressure 5 p.s.i.).

(b) Isolation Step:

The fermented broth prepared in the above step, which is adjusted to pH 10.5 with 10% sodium hydroxide, is centrifuged to give 145 L of supernatant. Adjusted to pH 4.0, the supernatant is applied to a column charged with 13 L of Dowex 50×2 ($Na^+$type) (Dow Chemical Co.), washed with 70 L of water, and eluted with 40 L of 30% acetone water containing 1% triethylamine. The fractions showing activity by the pulp disc dispersion method employing *Bacillus subtilis* are collected (22 L), adjusted to pH 5.0, and then condensed by evaporating acetone under reduced pressure. The resultant is applied to a column of 2 L of HP-20 (Mitsubishi Chemical Industries Co., Ltd.), washed with 20 L of water and eluted with 50% acetone water. The active fractions are collected (6 L), condensed under reduced pressure, and lyophilized to give 35.6 g of the crude powder of PA-42867.

(c) Purification Step: PA-42867-A and -B

The above crude powder (12 g) is dissolved in 150 ml of 0.01 N hydrochloric acid, and applied to a column of 100 ml of MCI GEL CHP-20P (Mitsubishi Chemical Industries Co.). The column is eluted with 0.01 N hydrochloric acid as tracing out the content of PA-42867 with HPLC. The fractions containing PA-42867-A and -B are adjusted to pH 7.0 and chromatographed again with CHP-20P column. The fractions containing PA-42867-A and -B are applied to the column, washed well with 15% methanol water, and eluted with 15% methanol-0.005 N hydrochloric acid, to give the fraction containing PA-42867-A and the fraction containing PA-42867-B.

The fraction containing PA-42867-A is adjusted to pH 7.0 and condensed. For the purpose of decoloration, the resultant is applied to a column of 10 ml of CHP-20P and then eluted with dilute hydrochloric acid (pH 5.0) to give the fraction containing PA-42867-A, which is condensed and lyophilized to give 571 mg of the residue (70% purity). After 571 mg of this residue is dissolved in water and adjusted to pH 5.0 by adding dilute hydrochloric acid, the solution is applied to a column of 10 ml of CHP-20P and eluted with water to give the fraction of PA-42867-A, which is adjusted to pH 7.0 and condensed. The resultant is applied again to a column of 10 ml of CHP-20P (stabilized with 0.05 M phosphate buffered saline (pH 7.0)) for the purpose of desalting, washed with 0.05 M phosphate buffered saline (pH 7.0) and then with water, and eluted with 50% methanol water to give the fraction of PA-42867-A, which is condensed and lyophilized to give 256 mg of PA-42867-A (95% purity).

The fraction containing PA-42867-B as noted above is adjusted to pH 7.0, condensed and lyophilized to give 683 mg of the residue. The residue (683 mg) of PA-42867-B dissolved in water is adjusted to pH 4.0 by adding dilute hydrochloric acid, applied to a column of 5 ml of CHP-20P for the purpose of decoloration and eluted with dilute hydrochloric acid (pH 4.0) to give the fraction of PA-42867-B, which is adjusted to pH 7.0 and condensed. The resultant is applied to Packed Column RQ-2 (Fujigeru Hanbai K.K.) and eluted with 7% acetonitrile-0.05 M phosphate buffered saline (pH 4.9) and then with 8% acetonitrile-0.05 M phosphate buffered saline (pH 4.9) while purity of PA-42867-B is being traced with HPLC. The fractions showing more than 95% purity are collected, adjusted to pH 7.0 and condensed. The resultant is applied to a column of 10 ml of CHP-20P (stabilized with 0.05 M phosphate buffered saline (pH7.0)) for desalting, washed with water and eluted with 50% methanol water to give the fractions containing PA-42867-B, which are condensed and lyophilized to give 102 mg of PA-42867-B (98% purity).

(d) Purification Step: des-(4-epi-vancosaminyl)-PA-42867-A and des-(4-epi-vancosaminyl-0-glucosyl)-PA-42867-A Precisely 2.00 g of crude product (containing 53% of PA-42867-A and 9% of PA-42867-B) obtained in the above step (b) is dissolved in 200 ml of 20% hydrochloric acid (Wako Pure Chemical Industries, Ltd., for precision analysis), and the solution is stirred for 16 hours with ice-chilling (0° to 1° C.) under a nitrogen atmosphere. To the reaction solution, 6 N sodium hydroxide (about 204 ml) is added to adjust to pH 9.2. The solution is applied to MCI GEL CHP20P (200 to 400 mesh, 100 ml), and eluted with successive, water (600 ml), 0.01 N hydrochloric acid (450 ml), water (450 ml), 25% methanol water (450 ml), 50% methanol water (400 ml), methanol (400 ml), and 50% methanol—0.005 N hydrochloric acid (400 ml).

By the fraction check with HPLC (Nucleosil 300-7C18, 4.6φ×250 mm, 10% acetonitrile-0.05 M PBS (pH 3.5), flow rate 1 ml/min., 220 nm UV detection), fraction A (0.01 N hydrochloric acid- and water-elution portions) and fraction B (50% methanol-, methanol-, and 50% methanol-0.005 N hydrochloric acid-elution portions) are obtained.

Fraction B is concentrated, adjusted to pH 3.5, applied to MCI GEL CHP-20P (200 to 400 mesh, 10 ml), and eluted with successive, 300 ml of water (adjusted to pH 4.0 by hydrochloric acid water, about 10$^{-4}$ N hydrochloric acid), 100 ml of 15% methanol water (pH 4.0), 100 ml of 30% methanol water (pH 4.0), 100 ml of 50% methanol water (pH 4.0), 50 ml of methanol, and 50 ml of 50% methanol-0.005 N hydrochloric acid to obtain fraction C (water (pH 4.0)-elution portion) and fraction D (50% methanol-water (pH 4.0)-elution portion).

Fractions A and C are put together, concentrated, adjusted to pH 7.0, and desalted by using MCI GEL CHP-20P (200 to 400 mesh, 10 ml); eluted with successive, water (100 ml), 25% methanol water (100 ml), 50% methanol water (100 ml), methanol (100 ml), and 50% methanol-0.005 N hydrochloric acid (50 ml) to obtain fraction E (not-desalted portion) and fraction F (desalted portion). Fraction E (not-desalted portion) is desalted again in the same conditions to obtain fraction G (desalted portion).

In water (39 ml) is dissolved 800 mg of the sediments of obtained fractions F and G (after concentrating each fraction, methanol is added thereto to form sediment) with heating, and methanol (39 ml) is added thereto for recrystallization to obtain 557 mg of crystals (drying under reduced pressure for 1.5 hours at 30° C. in the presence of phosphrous pentoxide) of des-(4-epi-vancosaminyl)PA-42867-A (HPLC 93% purity, yield 46.0%).

Separately, from crystal mother liquor and sediment forming mother liquor, 350 mg of freeze-dried product is obtained [des-(4-epi-vancosaminyl)PA-42867-A, HPLC 91% purity, yield 28.3%].

By similarly desalting fraction D, 30 mg of freeze-dried product is obtained [des-(4-epi-vancosaminyl-0-glucosyl)PA-42867-A, HPLC 93% purity, yield 2.8%].

Precisely 100 mg of PA-42867-A of 90% purity obtained in the same manner as in the above step (c) is dissolved in 10 ml of 20% hydrochloric acid and stirred for 10 minutes with heating in an oil bath at 40° to 45° C. under a nitrogen atmosphere. The reaction solution is adjusted to pH 9.2 with 6 N sodium hydroxide, applied to MCI GEL CHP-20P (200 to 400 mesh, 10 ml) and eluted with successive, water (100 ml), 0.01 N hydrochloric acid (50 ml), water (50 ml), 25% methanol (50 ml), 50% methanol (50 ml), methanol (50 ml) and 50% methanol-0.005 N hydrochloric acid (50 ml).

By checking the fraction with HPLC (Nucleosil 300-7C18, 10% acetonitrile-0.05 M PBS (pH 3.5), 220 nm UV detection), fraction I (0.01 N hydrochloric acid- and water-elution portions) and fraction II (50% methanol-, methanol-, and 50% methanol-0.005 N hydrochloric acid-elution portions) are obtained.

Fraction II is concentrated, adjusted to pH 3.5, applied to MCI GEL CHP-20P (200 to 400 mesh, 10 ml), and eluted with successive, 50 ml of water (pH 4.0), 15% methanol-water (pH 4.0), 30% methanol-water (pH 4.0), 50% methanol-water (pH 4.0), 50 ml of methanol, and 50 ml of 50% mehtanol-0.005 N hydrochloric acid, to obtain fraction III [water (pH 4.0)-elution portion] and fraction IV [50% methanol-water (pH 4.0)-, and 50% methanol-0.005 N hydrochloric acid-elution portions].

Fractions I and III are put together, concentrated, adjusted to pH 7.0 and desalted by using MCI GEL CHP-20P (200 to 400 mesh, 5 ml) to obtain des-(4-epi-vancosaminyl)PA-42867-A by 31.5 mg (yield 38.6%).

Fraction IV is similarly desalted to give 36.3 mg (yield 50.1%) of des-(4-epi-vancosaminyl-0-glucosyl)-PA-42867-A.

The *Nocardia* sp. PA-42867 which produces PA-42867-A was deposited as *Nocardia orientalis* PA-42867 with the Fermentation Research Institute, Agency of the Industrial Science & Technology, Higashi 1-1-3, Tsukuba City, Ibaragi Prefecture, on Jan. 8, 1986 under accession No. Bikoken Kinki 8601 (FERM P-8601), and changed to the deposition according to the Budapest Treaty, on Dec. 4, 1986 (FERM BP-1230).

EXPERIMENT

PA-42867-A (Compound 1), des-(4-epi-vancosaminyl) PA-42867-A (Compound 2), and des-(4-epi-vancosaminyl-0-glucosyl)PA-42867-A (Compound 3) were subjected to anti-microorganism tests using *Clostridium perfringens*, and their growth promoting actions were measured on chicks.

1. Determination of MIC against Cl. perfringens

Eleven strains of Cl. perfringens derived from cows and chickens were used in the test. Determination of sensitivity was conducted under anaerobic culture conditions (gas pack method) by agar plate dilution method, using GAM agar medium (Nippon Suisan Kaisha, Ltd.). After culturing the microorganism for 24 hours at 37° C., the lowest concentration of the drug at which the growth of the microorganism was visually inhibited, i.e., a minimum inhibitory concentration (MIC) of the drug, was determined (Table 1).

In the in vitro screening of antibiotics, it is believed that possession of antimicrobial activity against gram-positive bacteria, especially *Cl. perfringens,* is an indicator of the growth-promoting activity of the drug tested (Poultry Science 62, 1633～1638, 1983; Poultry Science 63, 2036～2042, 1984).

TABLE 1

Determination of MIC against Cl. perfringens

| Strain | Origin | MIC(μg/ml) Compound 1 | Compound 2 | Compound 3 |
|---|---|---|---|---|
| NCTC-10239 | Cow | 0.39 | 1.56 | 0.78 |
| FC 2208/75 | Cow | 0.39 | 1.56 | 0.78 |
| S-79 | Cow | 0.39 | 0.78 | 0.39 |
| CW-1970 | Cow | 0.39 | 1.56 | 0.78 |
| 6B-10 | Cow | 0.2 | 1.56 | 0.78 |
| NCTC-8239 | Cow | 0.39 | 1.56 | 0.78 |
| NCTC-8798 | Cow | 0.39 | 1.56 | 0.78 |
| SP07 | Chiken | 0.39 | 1.56 | 0.78 |
| 9C-02 | Chiken | 0.2 | 1.56 | 0.78 |
| 3C-01 | Chiken | 0.39 | 1.56 | 0.78 |
| 02441 | Chiken | 0.39 | 1.56 | 0.78 |

Compound 1: PA-42867-A
Compound 2: Des-(4-epi-vancosaminyl)PA-42867-A
Compound 3: Des-(4-epi-vancosaminyl-O—glucosyl)PA-42867-A 2. Growth promoting effect on chicks Growth promoting effect of PA-42867-A on chicks (8 days of age, Abaeker species) was determined using a known antibiotic, Thiopeptin, as a control. PA-42867-A and Thiopeptin were added to an antibiotic-free feed mash (crude protein content (CP): 18%) at a concentration of 20 ppm, and the chicks were raised for 10 days with the resulting feed according to the battery method. Specifically describing the method of experiment, newly hatched chicks were fed until 8 days of age with a feed ration of 23% CP by the flat feeding method, at which time the chicks were divided into three groups each containing 25–26 chicks (males and females, 12–13 chicks each) so that the average weights of the chicks in all groups were nearly the same. PA-42867-A group received 20 ppm of the antibiotic a day for 10 days, Thiopeptin group received 20 ppm for 10 days, and the control group received antibiotic-free feed of 18% CP for 10 days. The above feeding was conducted after dividing the chicks in each of these groups into sub-groups of 6–7 chicks and putting each sub-group in a cage (435×600×410 mm). The feeding was conducted for 10 days (until 18 days of age) at an environmental temperature of 26°±2° C. The effectiveness of the drug was evaluated based on the body weight gain and the feed efficiency observed during the 10 days period of the experiment. The results are as shown in Table 2.

TABLE 2

Growth Promoting Effect on Chicks

| Experimental group | Number of chicks | Body weight gain* (g) Mean value ± standard error | (index) | Feed efficiency |
|---|---|---|---|---|
| no antibiotic | 25 | 301.9 ± 6.46 | (100.0) | 1.70 |
| Thiopeptin (20 ppm × 10 days) | 26 | 313.7 ± 8.80 | (103.9) | 1.58 |
| PA-42867-A (20 ppm × 10 days) | 25 | 332.0 ± 6.71 | **(110.0) | 1.53 |

*Difference between the body weight at the end of the experiment (18 days of age) and the initial weight.
**P < 0.01 (T test)

As compared with the control group which received no antibiotic, and with the group which received Thiopeptin, the group which received PA-42867-A showed a significantly high body weight gain ($p<0.01$). The PA-42867-A group and Thiopeptin group showed better results in feed efficiency as compared with the group raised with the antibiotic-free feed.

In the same manner, another growth promoting tests were conducted on des-(4-epi-vancosaminyl)PA-42867-A and des-(4-epi-vancosaminyl-0-glucosyl)PA-42867-A by giving 20 ppm of the test drug to chicks of 8–21 days of age for 13 days, using Thiopeptin as a control.

The newly hatched chicks were fed until eight days of age with a feed mash (crude protein content (CP):23%) without addition of any antibiotic by means of the flat feeding. Then, the chicks were divided into four groups each containing 24 chicks (males and females, 12 each). Each group was placed in four cages after dividing into four unisexual sub-groups, each consisting of 6–7 chicks, and raised for 13 days with an animal feed of CP 18% with or without antibiotics. Thus, each of four groups received 20 ppm of des-(4-epi-vancosaminyl)PA-42867-A, 20 ppm of des(4-epi-vancosaminyl-0-glucosyl)PA-42867-A, 20 ppm of Thiopeptin, and no antibiotic, respectively.

Body weight gain and feed efficiency were measured on the 10th and the 13th day. The test results are shown in Table 3.

Growth promotion was observed in the groups which received antibiotics, as compared with the group which received no antibiotic.

TABLE 3

Growth Promoting Effect on Chicks

| Experimental group | Number of chicks | Body weight gain (g) ± standard error 10 days | 13 days | Feed efficiency 10 days | 13 days |
|---|---|---|---|---|---|
| No antibiotic* | 24 | 312.1 ± 7.7 (100)** | 425.8 ± 9.5 (100) | 1.69 | 1.76 |
| Compound 1 | 24 | 328.9 ± 6.3 (105.4) | 442.6 ± 7.8 (103.9) | 1.54 | 1.66 |

TABLE 3-continued

| | Growth Promoting Effect on Chicks | | | | |
|---|---|---|---|---|---|
| | Number of | Body weight gain (g) ± standard error | | Feed efficiency | |
| Experimental group | chicks | 10 days | 13 days | 10 days | 13 days |
| (20 ppm × 13 days) Compound 2 (20 ppm × 13 days) | 24 | 324.6 ± 8.3 (104.0) | 447.4 ± 11.5 (105.0) | 1.62 | 1.66 |
| Thiopeptin (20 ppm × 13 days) | 24 | 319.5 ± 7.5 (102.4) | 445.5 ± 11.1 (104.6) | 1.61 | 1.70 |

*Control group received an animal feed only containing 18% crude protein.
**Numerals in ( ) shows a comparative index of each group when the weight gain of the control group is regarded as 100.
Compound 1: Des-(4-epi-vancosaminyl)PA-42867-A
Compound 2: Des-(4-epi-vancosaminyl)-O—gulcosyl)PA-42867-A The animal feeds according to the present invention, which promote animal growth, can be prepared in conventional manner and are illustrated by the following examples. However, the invention should not be construed to be limited thereto.

EXAMPLE 1

| Corn | 46.45% |
|---|---|
| Milo | 15.00% |
| Soybean meal | 5.00% |
| Fish meal | 3.00% |
| Defatted rice bran | 25.00% |
| Alfalfa | 3.00% |
| Calcium carbonate | 1.00% |
| Calcium phosphate | 0.70% |
| Sodium chloride | 0.40% |
| Mixture of Vitamins A, D, and E | 0.05% |
| *Mixture of inorganic salts | 0.10% |
| **Mixture of vitamin B group | 0.10% |
| PA-42867-A | 10 ppm |

The above ingredients are mixed well to give an animal feed of the invention for poultry or swine.
*Mixture of inorganic salts: Manganese sulfate, zinc sulfate, copper sulfate, cobalt sulfate, and potassium iodide.
**Mixture of vitamin B group: Vitamin $B_1$, vitamin $B_2$, vitamin $B_6$, vitamin $B_{12}$, biotin, folic acid, and calcium pantothenate.

EXAMPLE 2

| Corn | 41.00% |
|---|---|
| Milo | 25.00% |
| Soybean meal | 19.10% |
| Fish meal | 8.00% |
| Oil and fat | 4.00% |
| Calcium carbonate | 1.40% |
| Calcium phosphate | 0.85% |
| *Mixture of vitamins and inorganic salts | 0.26% |
| Methionine | 0.10% |
| Sodium chloride | 0.29% |
| PA-42867-A | 20 ppm |

The above ingredients are mixed well to give an animal feed of the invention for poultry or swine.
*Mixture of vitamins and inorganic salts: Vitamin A, vitamin $D_3$, vitamin E, vitamin $B_1$, vitamin $B_2$, vitamin $B_6$, vitamin $B_{12}$, calcium pantothenate, nicotinamide, vitamin $K_4$, choline chloride, magnesium sulfate, iron sulfate, copper sulfate, zinc sulfate, cobalt sulfate, and potassium iodide.

EXAMPLE 3

| Corn | 78% |
|---|---|
| Soybean meal | 9% |
| Fish meal | 10% |
| Fat | 3.9% |
| Crude fiber | 2.4% |
| Crude ash | 5.1% |
| Calcium | 1.07% |
| Phosphoric acid | 0.73% |
| Mixture of alfalfa meal, sodium chloride, and calcium carbonate | 3.0% |
| PA-42867-A | 20 ppm |

The above ingredients are mixed well to give an animal feed of the invention for poultry or swine.

EXAMPLE 4

Des-(4-epi-vancosaminyl)PA-42867-A or des-(4-epi-vancosaminyl-0-glucosyl)PA-42867-A is mixed with other ingredients in the same manner as in Examples 1, 2 or 3 mentioned above, to give an animal feed of the invention for poultry or swine.

What is claimed is:

1. A method for growth promotion of animals which comprises administering to said animals an effective amount of a compound of the formula I:

[Chemical structure of formula I]

wherein R is

[Chemical structure] or [Chemical structure]

or a salt thereof in admixture with conventional carriers and/or ingredients for an animal feed.

* * * * *